(12) United States Patent
Cheung et al.

(10) Patent No.: US 10,933,043 B2
(45) Date of Patent: *Mar. 2, 2021

(54) METHODS OF TREATING NEURODEVELOPMENTAL DISEASES AND DISORDERS

(71) Applicants: Deakin University, Victoria (AU); The Florey Institute of Neuroscience and Mental Health, Victoria (AU)

(72) Inventors: Steve Cheung, Victoria (AU); Wah Chin Boon, Victoria (AU)

(73) Assignees: Deakin University, Victoria (AU); The Florey Institute of Neuroscience and Mental Health, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/282,880

(22) Filed: Feb. 22, 2019

(65) Prior Publication Data

US 2019/0314315 A1   Oct. 17, 2019

Related U.S. Application Data

(63) Continuation of application No. 15/892,144, filed on Feb. 8, 2018, now Pat. No. 10,251,856, which is a continuation of application No. 15/316,110, filed as application No. PCT/AU2015/050310 on Jun. 5, 2015, now Pat. No. 9,925,163.

(30) Foreign Application Priority Data

Jun. 6, 2014   (AU) ................................ 2014902173

(51) Int. Cl.
| | | |
|---|---|---|
| *A61K 31/20* | (2006.01) | |
| *A61K 31/201* | (2006.01) | |
| *A61K 35/644* | (2015.01) | |

(52) U.S. Cl.
CPC .......... *A61K 31/201* (2013.01); *A61K 35/644* (2013.01)

(58) Field of Classification Search
CPC .................................................. A61K 31/20
USPC ....................................................... 514/560
See application file for complete search history.

(56) References Cited

U.S. PATENT DOCUMENTS

| 8,557,864 B2 | 10/2013 | Iinuma et al. |
| 9,428,477 B2 | 8/2016 | Iinuma et al. |
| 9,925,163 B2 | 3/2018 | Cheung et al. |
| 1,025,185 A1 | 4/2019 | Cheung et al. |
| 2013/0289277 A1 | 10/2013 | Tsujimura |
| 2015/0087823 A1 | 3/2015 | Iinuma et al. |

FOREIGN PATENT DOCUMENTS

| CN | 103816307 A | 5/2014 |
| EP | 2311472 A1 | 4/2011 |
| JP | H0967252 A | 3/1997 |
| WO | WO-2007130581 A2 | 11/2007 |
| WO | WO-2015184509 A1 | 12/2015 |
| WO | WO-2017093807 A1 | 6/2017 |

OTHER PUBLICATIONS

Berge et al. Pharmaceutical Salts. Journal of Pharmaceutical Sciences 66(1):1-19 (Jan. 1977).
Hattori et al. Royal jelly and its unique fatty acid, 10-hydroxy-trans-2-decenoic acid, promote neurogenesis by neural stem/progenitor cells in vitro. Biomed Res 28(5):261-266 (2007).
Hill et al. Estrogen Deficient Male Mice Develop Compulsive Behavior. Biol Psychiatry 61:359-366 (2007).
Hussman et al. A noise-reduction GWAS analysis implicates altered regulation of neurite outgrowth and guidance in autism. Mol Autism 2:1-16 (2011).
Ito et al. Antidepressant-like activity of 10-hydroxy-trans-2-decenoic Acid, a unique unsaturated Fatty Acid of royal jelly, in stress-inducible depression-like mouse model. Evid Based Complement Alternat Med 2012:139140 (6 pgs.) (2012).
Makino et al. 2-Decenoic acid ethyl ester possesses neurotrophin-like activities to facilitate intracellular signals and increase synapse-specific proteins in neurons cultured from embryonic rat brain. Biomed Res 31(6):379-386 (2010).
Makino et al. Anxiolytic-like effect of trans-2-decenoic acid ethyl ester in stress-induced anxiety-like model mice. Biomed Res 34(5):259-267 (2013).
PCT/AU2015/050310 International Preliminary Report on Patentability dated Dec. 15, 2016.
PCT/AU2015/050310 International Search Report and Written Opinion dated Aug. 14, 2015.
PCT/IB2016/001853 International Search Report and Written Opinion dated Mar. 31, 2017.
Pyrzanowska et al. Long-term administration of Greek Royal Jelly improves spatial memory and influences the concentration of brain neurotransmitters in naturally aged Wistar male rats. J Ethnopharmacol 155(1):1-8 (2014).
Pyrzanowska et al. Short-term administration of Greek Royal Jelly changes brain serotonergic transmission in aged rats. Pharmacol Rep 65(Suppl 1):76 (2013).
Salem. Modulatory effects of Trifolium pretense extract and Royal jelly on the function of hypothalamic-pituitary-ovarian axis in ovariectomized rats. International Journal of Pharmacy and Pharmaceutical Sciences 5(3):593-597 (2013).

(Continued)

*Primary Examiner* — Raymond J Henley, III
(74) *Attorney, Agent, or Firm* — Kilpatrick Townsend & Stockton LLP

(57) ABSTRACT

The present invention relates generally to methods for the treatment and/or prophylaxis of neurological diseases and disorders involving administration of trans 10-HDA. In particular, the methods of the present invention are useful in the treatment and/or prophylaxis of acquired or progressive neurodevelopmental disorders and conditions in mammals. More particularly, methods are taught herein for the treatment and/or prophylaxis of diseases and disorders such as autism spectrum disorders.

12 Claims, 10 Drawing Sheets

(56) References Cited

OTHER PUBLICATIONS

Shibata et al. A novel 2-decenoic acid thioester ameliorates corticosterone-induced depression—and anxiety-like behaviors and normalizes reduced hippocampal signal transduction in treated mice. Pharmacol Res Perspect 3(2):e00132 (12 pgs.) (2015).

Sugiyama et al. Royal jelly acid, 10-hydroxy-trans-2-decenoic acid, as a modulator of the innate immune responses. Endocr Metab Immune Disord Drug Targets 12(4):368-376 (2012).

Tearing her hair out: "At last I might be able to conquer this destructive habit". Express Blog Post available at http://www.express.co.uk/life-style/health/432881/Tearing-her-hair-out-At-last-I-might-be-able-to-conquer-this-destructive-habit (4 pgs.) (Retrieved Nov. 16, 2016).

U.S. Appl. No. 15/316,110 Office Action dated Jul. 21, 2017.

U.S. Appl. No. 15/892,144 Office Action dated Jun. 6, 2018.

METHODS OF TREATING NEURODEVELOPMENTAL DISEASES AND DISORDERS

CROSS REFERENCE TO RELATED APPLICATIONS

This application is a Continuation Application of U.S. application Ser. No. 15/892,144, filed Feb. 8, 2018 (now U.S. Pat. No. 10,251,856, issued Apr. 9, 2019), which is a Continuation Application of U.S. application Ser. No. 15/316,110, filed Dec. 2, 2016 (now U.S. Pat. No. 9,925,163, issued Mar. 27, 2018), which is a U.S. National Phase Application of PCT/AU2015/050310, filed Jun. 5, 2015, which claims the benefit of Australian Application No. 2014902173, filed Jun. 6, 2014, all of which are incorporated herein by reference in their entirety.

TECHNICAL FIELD

The present invention relates generally to methods for the treatment and/or prophylaxis of neurological diseases and disorders. In particular, the methods of the present invention are particularly useful in the treatment and/or prophylaxis of acquired or progressive neurodevelopmental disorders and conditions in mammals. More particularly, methods are taught herein for the treatment and/or prophylaxis of diseases and disorders such as autism spectrum disorders.

BACKGROUND

Neurological diseases and disorders represent potentially debilitating conditions and can affect people of all ages. Such diseases may be acquired or congenital. Neurodevelopmental disorders represent a subset of disorders characterised by impairments of the growth and development of the brain or central nervous system. They are associated with widely varying degrees of difficulty which may have significant mental, emotional, physical, and economic consequences for individuals.

Acquired neurological diseases or disorders may be traumatic, that is, wherein an external force causes damage to the brain; or an injury resulting from, for example, infection, disease, toxicity, oxygen or glucose deprivation. A congenital neurological disorder typically exists at birth or before birth and may be the result of genetic abnormalities, the intrauterine environment, errors of morphogenesis, infection, or a chromosomal abnormality. Neurodevelopmental disorders may be acquired or congenital. Neurodevelopmental diseases or disorders in accordance with the present invention may include, for example, autism spectrum disorders.

Autism spectrum disorders (ASD) are a complex group of sporadic and familial developmental disorders affecting 1 in 150 births and characterized by abnormal social interaction, impaired communication, impaired social interaction, and restricted, repetitive patterns of behaviour, interests or activities. ASD includes autism Autistic Disorder, Asperger's Disorder, Childhood Disintegrative Disorder and Pervasive Developmental Disorder-Not Otherwise Specified (PDD-NOS) and Rett syndrome. The etiology of ASD is poorly understood and no single specific cause has been identified. However, certain risk factors are thought to contribute to the development of ASD, including genetics, prenatal and perinatal factors, neuroanatomical abnormalities, and environmental factors. For example, a genetic basis is evidenced by the greater than 70% concordance in monozygotic (MZ) twins and elevated risk in siblings compared to the population.

Autism spectrum disorders are highly variable neurodevelopmental disorders; distinguished not by a single symptom, but by a multitude of characteristic symptoms that typically first appear during infancy or childhood. Related symptoms may begin after the age of six months, becoming established around the age of two or three years, and continue through adulthood.

ASD is more common in males than females, with a ratio of approximately 5.5:1. Surprisingly, mutations in the only sex-linked ASD associated gene Neuroligin 3 are rare in ASD patients and no other sex-linked gene has so far been identified in ASD linkage or GWAS studies. However, the sexually dimorphic brain expressing CYP19A1 (encodes aromatase, the enzyme that synthesises oestrogens) gene is only 19 Mb away from a suggestive ASD linkage at 15q23-q25 7. Recently, it was reported that aromatase expression was lowered in ASD patients. Furthermore, it has been reported that CYP19A1 is a candidate gene for human cognitive functions implicated in reading, speech and language.

To date, there is no cure for ASD and a single, effective treatment has not been identified. Current treatments for autism spectrum disorders aim to increase quality of life and functional independence as well as reduce associated deficits and family distress. In certain cases, educational or behavioural therapies may improve functioning and decrease symptom severity. Outside of behavioural therapies, a number of different medications have been used, with varying degrees of success, to specifically reduce symptoms of ASD that interfere with social integration and function when behavioural treatments fail. Such medications include psychoactive drugs, anticonvulsants, antidepressants, stimulants, and antipsychotics. However, ASD patients often respond atypically to medications or the prescribed medications may have other adverse side effects. No single medication is known to relieve or reverse the core symptoms of ASD, such as social and communication impairments.

Accordingly, there is an on-going need to develop new therapeutic agents or methods of treating and/or preventing neurodevelopmental disorders such, as ASD.

SUMMARY

The applicants of the present application have surprising found that 10-HDA, compositions containing 10-hydroxy-2-decenoic acid (10-HDA), and pharmaceutically acceptable salts thereof, offer an effective therapy for the treatment and/or prophylaxis of diseases or disorders of the central nervous system, in particular, neurodevelopmental disorders, such as autism spectrum disorders.

10-HDA, also referred to as queen bee acid, is a fatty acid and key component of royal jelly; a honey bee secretion used in the nutrition of larvae and adult queens. Trans or (E) 10-HDA has the following structure:

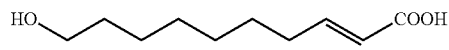 [SMILES: O=C(O)/C=C/CCCCCCCO]

This is in contrast to the structure of cis or (Z) 10-HDA, which has the structure:

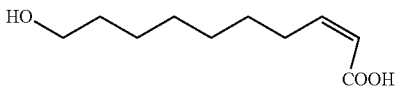 [SMILES: O=C(O)/C=C\CCCCCCCO]

Throughout this specification reference to 10-HDA is intended to mean reference to the trans or (E) isomeric form of the compound, which the inventors have determined to be the active form of the compound in the context of the present invention.

In one aspect of the invention, there is provided a method for the treatment and/or prophylaxis of disease or disorder of the central nervous system, comprising administering to a mammal in need thereof an effective amount of 10-hydroxy-2-decenoic acid or a pharmaceutically acceptable salt thereof.

In one or more embodiments, the central nervous system disease or disorder may be a neurodevelopmental disease or disorder, including an acquired neurodevelopmental disease or disorder, a congenital neurodevelopmental disease or disorder, or a related condition.

Examples of diseases or disorders relevant to the present invention include: Autism spectrum disorders, fetal alcohol spectrum disorder, motor disorders including developmental coordination disorder, stereotypic movement disorder and the tic disorders including Tourette syndrome, congenital injuries such as those that cause cerebral palsy, communication, speech and language disorders, genetic disorders such as fragile-X syndrome, down syndrome, and attention deficit hyperactivity disorder.

In one or more embodiments, the neurodevelopmental disorder may be an autism spectrum disorder, in particular an autism spectrum disorder selected from the group consisting of Autistic Disorder, Asperger's Disorder, Childhood Disintegrative Disorder and Pervasive Developmental Disorder-Not Otherwise Specified, and Rett syndrome.

In other aspects, 10-hydroxy-2-decenoic acid or a pharmaceutically acceptable salt thereof in accordance with the present invention may be administered as a composition. For example, the composition may comprise royal jelly, an extract of royal jelly, or a composition derived from royal jelly.

In still other aspects, the present invention provides the use of 10-hydroxy-2-decenoic acid or a pharmaceutically acceptable salt thereof in the preparation of a medicament for the treatment and/or prophylaxis of neurodevelopmental diseases or disorders, including ASD.

Unless defined otherwise, all technical and scientific terms used herein have the same meanings as commonly understood by one of ordinary skill in the art to which this invention belongs.

The reference to any prior art in this specification is not, and should not be taken as, an acknowledgment or any form of suggestion that that prior art forms part of the common general knowledge.

DETAILED DESCRIPTION

Figure 1:
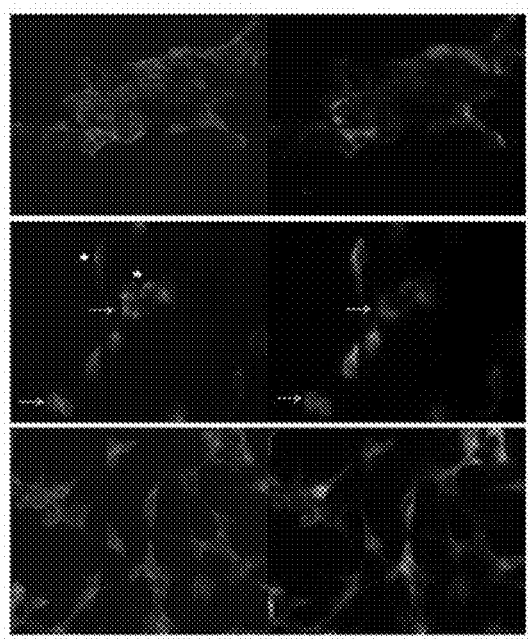
FIG. 1: Effects of BPA and 10-HDA on aromatase expression in human neuroblastoma SH-SY5Y cells. Under normal conditions, SH-SY5Y cells express aromatase which is a membrane bound protein in endoplasmic reticulum, and appears as green punctate staining eventually distributed within the cell by immunohistochemistry. In the presence of 25 µg/L bisphenol A the aromatase became aggregates. The effects of bisphenol A can be ameliorated by addition of 10HDA. (a) +0 µg/L BPA (Vehicle)—Clear staining of aromatase (green) evenly distributed in the cytoplasm and along the neurites, as tiny "dots". A lot of healthy cells evenly distributed over the surface area of the coverslip. B-tubulin (red) is highly expressed throughout the cytoplasm and neurites. (b) +25 µg/L BPA—Some populations of cells are starting to lose their neurites (yellow arrows). A decrease in 13-tubulin expression was also observed in most cells that have lost their neurites. Aromatase aggregates start to form in these cells that have lost their neurites (asterix). (c) +25 µg/L BPA+1 mM 10 HDA—Good neurite growth and even aromatase distribution throughout the cytoplasm was observed. The addition of 10HDA ameliorates the effects of BPA on the expression pattern of aromatase and neurites.

The present invention relates to methods of treating diseases or disorders of the central nervous system comprising administering to a mammal in need thereof an effective amount of 10-HDA.

The methods of the present invention advantageously provide a reduction of core symptoms of neurological disorder, in particular the symptoms associated with a neurodevelopmental disorder such as ASD. In some aspects, the methods of the present invention advantageously provide a reduction in the severity of symptoms of autism, for example, social interaction deficit.

Preferably the person is in need of such treatment, although the compound may be administered in a prophylactic sense.

References to a "neurodevelopmental condition", a "neurodevelopmental disorder" or a "neurodevelopmental disease", are used interchangeably, and should be understood as a reference to a condition characterised by neurologically based cognitive, emotional and behavioural disturbances.

In one embodiment, said neurodevelopmental condition is a condition which is characterised by one or more symptoms of ASD, including autism.

The term Autism Spectrum Disorder (ASD), as used herein, would be clear to persons skilled in the art and includes Autistic Disorder, Asperger's Disorder, Childhood Disintegrative Disorder and Pervasive Developmental Disorder-Not Otherwise Specified (PDD-NOS) and Rett syndrome, as defined in the Diagnostic and Statistical Manual of Mental Disorders 5 (DSM-5) published in May 2013. The Diagnostic and Statistical Manual of Mental Disorders 5 outlines diagnose of ASD by the presence of three key diagnostic criteria:
   a) Impaired social functioning. Withdrawal from or avoidance of social groups;
   b) Communication deficits: Including failure to develop speech, use of stereotyped or delayed echolalia, and difficulties maintaining conversations; and
   c) Repetitive stereotyped behaviour. Excessive and redundant activities.

Reference to "symptoms characteristic of ASD" should be understood as a reference to any one or more symptoms which may occur in an individual suffering from ASD. These symptoms may be evident throughout the disease course or they may be evident only transiently or periodically. For example, an individual may exhibit severe impaired social function in response to specific environmental cues or stressors. It should also be understood that the subject symptoms may not necessarily be exhibited by all individuals suffering from ASD. For example, some individuals may suffer from communications deficits such as failure to develop speech. However, for the purpose of the present invention, any such symptoms, irrespective of how many or few ASD patients ever actually exhibit the given symptom, are encompassed by this definition. Without limiting the present invention to any one theory or mode of action, the symptoms that are most commonly associated with ASD include impaired social function and communication deficits.

Examples of impaired social function characteristic of ASD include, but are not limited to:
   Does not respond to name by 12 months of age;
   Avoids eye-contact;
   Prefers to play alone;
   Does not share interests with others;
   Only interacts to achieve a desired goal;
   Has flat or inappropriate facial expressions;
   Does not understand personal space boundaries;
   Avoids or resists physical contact;
   Is not comforted by others during distress; or
   Has trouble understanding other people's feelings or talking about own feelings.

Examples of communication deficits characteristic of ASD include, but are not limited to:
   Delayed speech and language skills;
   Repeats words or phrases over and over (echolalia);
   Reverses pronouns (e.g., says "you" instead of "I");
   Gives unrelated answers to questions;
   Does not point or respond to pointing;
   Uses few or no gestures (e.g., does not wave goodbye);
   Talks in a flat, robot-like, or sing-song voice;
   Does not pretend in play (e.g., does not pretend to "feed" a doll); or
   Does not understand jokes, sarcasm, or teasing.

With regard to repetitive motions, these include actions which may be repeated over and over again. They can involve one part of the body or the entire body or even an object or toy. For instance, people with an ASD might spend a lot of time repeatedly flapping their arms or rocking from side to side. They might repeatedly turn a light on and off or spin the wheels of a toy car. These types of activities have been described as self-stimulation or "stimming".

People with ASD often thrive on routine. A change in the normal pattern of the day can be very upsetting for an individual suffering from ASD. They might "lose control" and have a "melt down" or tantrum, especially where the environment is unfamiliar.

An individual suffering from ASD may develop routines that could be perceived as unusual or unnecessary. For example, an individual suffering from ASD may try to look in every window he or she walks by a building or might always want to watch a video from beginning to end, including the previews and the credits. Deviation from these types of routines may cause severe frustration and tantrums.

In addition to the fact that there may be significant variation between ASD patients in terms of which symptoms they exhibit, it should also be understood that there are other neurodevelopmental conditions and disorders which are also characterised by one or more of these symptoms. The social deficits and communication difficulties exhibited by ASD patients, for example, are also commonly observed in patients with foetal alcohol spectrum disorder or down syndrome. Accordingly, reference to a condition characterised by one or more symptoms characteristic of ASD should be understood as a reference to any neurodevelopmental condition which is characterised by the presence of one or more of these symptoms.

In one embodiment, said condition is a condition characterised by one or more symptoms of ASD.

In another embodiment, said condition is autism.

The present invention is predicated in part on recent reports that aromatase expression was lowered in ASD patients. In view of this, and without wishing to be bound by theory, it was postulated that an Aromatase Knockout mouse (ArKO) model may exhibit behavioural phenotypes reflective of some of the key diagnostic behaviours and symptoms of ASD, including, for example ASD-like behavioural disturbances. The inventors have demonstrated that the lack of a normal functioning aromatase will precipitate ASD-like behavioural disturbances in the in a male Aromatase Knockout mouse (ArKO) mouse, consistent with the observation that ASD is more common in males than females within human populations.

The behavioural phenotype exhibited by male ArKO mice was used as the basis for further comparative studies. In particular, the inventors have also examined the role of environmental exposure to Bisphenol A (BPA), employed in the preparation of polycarbonate plastics and epoxy resins, in the subsequent development of autistic-like behaviour. To this end, the ArKO mouse which exhibits ASD-like features, provided a comparative tool to examine the effects of exposure to BPA.

The term "mammal" as used herein includes humans, primates, livestock animals (e.g. horses, cattle, sheep, pigs, donkeys), laboratory test animals (e.g. mice, rats, guinea pigs), companion animals (e.g. dogs, cats) and captive wild animals (e.g. kangaroos, deer, foxes). Preferably, the mammal is a human.

For certain of the abovementioned conditions it is clear that the methods of the invention may be used prophylactically as well as for the alleviation of acute symptoms. Accordingly, references herein to "treatment" or the like are to be understood to include such prophylactic treatment, as well as treatment of acute conditions.

The term "indicative", as used herein, denotes an association or affiliation of a subject closely to a group or population of subjects who present, or likely to present, with the same or a similar clinical manifestations or response to the treatment. For example, the clinical manifestations of ASD are encompassed by symptoms of ASD.

One of skill in the art will be familiar with the difficulties in administering traditional antipsychotic and antidepressant medications, including lag phases and heightened anxiety in the initial stages of treatment before the antidepressant effects are seen. Thus, in certain embodiments, it is envisaged that 10-HDA, pharmaceutically acceptable salts or compositions comprising 10-HDA described herein may be administered to a person in need thereof as a substitute or replacement for traditional medication. In other embodiments, it is envisaged that 10-HDA, pharmaceutically acceptable salts or compositions comprising 10-HDA may be administered to a subject in need thereof as a supplement or adjunct to traditional medication. In still other embodiments, it is envisaged that 10-HDA or compositions comprising 10-HDA, or a pharmaceutically acceptable salts thereof, may be administered to a person in need thereof in the absence of adjunct therapy. In still other embodiments, it is envisaged that 10-HDA, compositions comprising 10-HDA, or pharmaceutically acceptable salts thereof, may be administered to a person in need thereof in conjunction with, or as an adjunct to, behavioural or cognitive therapies.

Replacing traditional medication with 10-HDA, compositions comprising 10-HDA, or pharmaceutically acceptable salts, may be advantageous, particularly where the traditional medication is associated with one or more adverse effects (e.g., sleepiness, tremors, anxiety, suicidal ideation, etc.). Examples of medication would be known to those skilled in the art and include, but are not limited to, selective serotonin re-uptake inhibitors (SSRI), antipsychotics, antidepressants, lithium and other mood stabilisers.

In other embodiments, the present compounds are administered to a subject in need thereof, together with traditional medication for a discrete period of time, to address symptoms such as psychosis, depression or anxiety, with the option of discontinuing treatment with the present extracts and isolated compounds whilst continuing with the traditional therapy. In still other embodiments, the person in need thereof may be treated with both the compounds described herein and one or more traditional medications (administered sequentially or in combination) for the duration of the treatment period. Such combination therapy may be particularly useful, for example, where an additive or synergistic therapeutic effect is desired.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of condition, or the amelioration of one or more symptoms (e.g., one or more discernible symptoms) of said condition (i.e., "managing" without "curing" the condition), resulting from the administration of one or more therapies (e.g., one or more therapeutic agents such as a compound or composition of the invention). In specific embodiments, the terms "treat", "treatment" and "treating" refer to the amelioration of at least one measurable physical parameter of a condition described herein. In other embodiments the terms "treat", "treatment" and "treating" refer to the inhibition of the progression of a condition described herein, either physically by, e.g., stabilization of a discernible symptom or physiologically by, e.g., stabilization of a physical parameter, or both.

The desired therapeutic activity, or effect, will typically depend on the condition being treated. For example, where the subject is being treated for schizophrenia, the therapeutic effect may be a reduction in at least one clinical symptom of schizophrenia, including, but not limited to, anxiety, suicidal thoughts, cognitive impairment, loss of appetite, mood, and/or inactivity. In the case where the subject is being treated for ASD, the therapeutic effect may be a reduction in at least one clinical symptom of ASD, including, but not limited to, reduction in impaired social function, stereotypy, repetitive behaviour and communication deficits.

The terms "preventing" and "prophylaxis" as used herein refer to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent", "preventing" and "prevention" with regard to a disorder or disease, refer to averting the cause, effects, symptoms or progression of a disease or disorder prior to the disease or disorder fully manifesting itself.

The compounds of the present invention are administered to the person in need thereof in a treatment effective amount. In some embodiments, a treatment effective amount is a therapeutically effective amount or a prophylactically effective amount. The term "therapeutically effective amount" as used herein means that amount of an active compound that elicits the biological or medicinal response in a tissue, system, animal or human that is being sought by a researcher, veterinarian, medical doctor, or other clinician. The therapeutically effective amount of the compound to be administered will be governed by such considerations, and is the minimum amount necessary to ameliorate, cure, or treat the disease or disorder or one or more of its symptoms. The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease or symptom) and secondary prophylaxis (whereby the disease or symptom has already developed and the patient is protected against worsening of this process).

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 100 g per kg of body weight per dosage. The dosage may be in the range of 1 µg to 10 g per kg of body weight per dosage, such as is in the range of 1 mg to 1000 mg per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 200 mg per kg of body weight per dosage, such as up to 50 mg per body weight per dosage.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

In certain embodiments, an effective amount of a compound for administration one or more times a day to a 70 kg adult human may comprise about 0.0001 mg to about 4000 mg, about 0.0001 mg to about 3000 mg, about 0.0001 mg to about 200 mg, about 0.001 mg to about 1500 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of compound per unit dosage form.

In certain embodiments, the extracts and/or compounds of the invention may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Compounds of the present invention may be administered in a single dose or a series of doses. While it is possible for the compound to be administered alone, in some embodiments it may be preferable to present it as a composition, preferably as a pharmaceutical composition. The formulation of such compositions is well known to those skilled in the art. Such a composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The compounds and associated pharmaceutical compositions of the present invention may be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another antipsychotic, anticonvulsant or antidepressant medication, an "effective amount" of the second agent will depend on the type of drug used. Suitable dosages are known for approved agents and can be adjusted by a person skilled in the art according to the condition of the subject, the type of condition(s) being treated and the amount of a compound, extract or composition being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

The phrase "combination therapy" as used herein, is understood to refer to administration of an effective amount, using a first amount of 10-HDA, a composition comprising 10-HDA or a pharmaceutically acceptable salt thereof as described herein, and a second amount of an additional suitable therapeutic agent.

In certain embodiments, 10-HDA, or a composition comprising 10-HDA as described herein, or a pharmaceutically acceptable salt thereof, and the additional therapeutic agent, are each administered in an effective amount (i.e., each in an amount which would be therapeutically effective if administered alone). In other embodiments, 10-HDA, or a composition comprising 10-HDA as described herein, or a pharmaceutically acceptable salt thereof, and the additional therapeutic agent are each administered in an amount which alone does not provide a therapeutic effect (a sub-therapeutic dose). In yet other embodiments, 10-HDA, or a composition comprising 10-HDA as described herein, or a pharmaceutically acceptable salt thereof, can be administered in an effective amount, while the additional therapeutic agent is administered in a sub-therapeutic dose. In still other embodiments, 10-HDA, or a composition comprising 10-HDA as described herein, or a pharmaceutically acceptable salt thereof, can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a person in need thereof.

Co-administration encompasses administration of the first and second amounts of therapeutic compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of 10-HDA, or a composition comprising 10-HDA, as described herein, or a pharmaceutically acceptable salt thereof, and a second amount of an additional therapeutic agent, they are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, 10-HDA, or a composition comprising 10-HDA as described herein, or a pharmaceutically acceptable salt thereof, and the second therapeutic agent can be administered in any order within about 24 hours of each other, within about 16 hours of each other, within about 8 hours of each other, within about 4 hours of each other, within about 1 hour of each other or within about 30 minutes of each other.

10-HDA, or a composition comprising 10-HDA, or a pharmaceutically acceptable salt thereof, in accordance with the invention may be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In particular embodiments, 10-HDA, or a composition comprising 10-HDA of the present invention are administered orally.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

Where a carrier is used, the carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous, and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

In some embodiments, where 10-HDA of the present invention is for oral administration, it may be prepared as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The 10-HDA may also be presented as a bolus, electuary or paste.

In some embodiments, where the 10-HDA is formulated as a tablet, the tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., inert diluent, preservative disintegrant (e.g., sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

In some embodiments, the 10-HDA, or compositions comprising 10-HDA, of the present invention may be in micro-encapsulated form with one or more excipients. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

In some embodiments, where the 10-HDA of the present invention is to be administered as a liquid dosage form for oral and parenteral administration, such a dosage form may include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the 10-HDA of the invention is mixed with solubilizing agents such as Cremophor™, alcohols, oils, modified oils, glycols, polysorbates, cyclodextrins, polymers, and mixtures thereof.

In some embodiments, where the 10-HDA, or a composition comprising 10-HDA, of the present invention is to be administered topically in the mouth, suitable dosage forms may include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

In some embodiments, where the 10-HDA, or composition comprising 10-HDA, of the present invention is to be administered topically to the skin, suitable dosage forms may include the dissolving or suspending the extract or component compound in any suitable carrier or base and may be in the form of lotions, gel, creams, pastes, ointments and the like. Suitable carriers include mineral oil, propylene glycol, polyoxyethylene, polyoxypropylene, emulsifying wax, sorbitanmonostearate, polysorbate 60, cetyl esters wax, cetearyl alcohol, 2-octyldodecanol, benzyl alcohol, and water. Transdermal patches may also be used to administer the extract or component compound of the invention.

In some embodiments, the 10-HDA, or composition comprising 10-HDA, of the present invention is for rectal administration, suitable dosage forms may include a suppository with a suitable base comprising, for example, cocoa butter, glycerin, gelatine or polyethylene glycol.

In some embodiments, where the 10-HDA, or composition comprising 10-HDA, of the present invention is for vaginal administration, suitable dosage forms may include pessaries, tampons, creams, gels, pastes, foams or spray formulations containing in addition to the active ingredient such carriers as are known in the art to be appropriate.

In some embodiments, where the 10-HDA, or composition comprising 10-HDA, of the present invention is for parenteral administration, suitable dosage forms may include aqueous and non-aqueous isotonic sterile injection solutions which may contain anti-oxidants, buffers, bacteri-cides and solutes which render the composition isotonic with the blood of the intended recipient; and aqueous and non-aqueous sterile suspensions which may include suspending agents and thickening agents. The compound may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described. An injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In certain embodiments, unit dosage compositions are those containing a daily dose or unit, daily sub-dose, as herein above described, or an appropriate fraction thereof, of the active ingredient.

It should be understood that in addition to the active agent 10-HDA, compositions comprising 10-HDA of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glycerylmonostearate or glyceryldistearate.

The phrase "pharmaceutically acceptable salt," as used herein, refers to pharmaceutically acceptable organic or inorganic salts of a provided compound. For use in medicine, the salts of the provided compounds will be pharmaceutically acceptable salts. Other salts may, however, be useful in the preparation of provided compounds or of their pharmaceutically acceptable salts. Pharmaceutically acceptable salts are well known in the art. For example, Berge et al., describe pharmaceutically acceptable salts in detail in *J. Pharm. Sci.* (1977) 66:1-19, incorporated herein by reference in its entirety. A pharmaceutically acceptable salt involves the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. When multiple charged atoms are present in the parent drug, its pharmaceutically acceptable salts will have multiple counter ions and these can be several instances of the same counter ion or different counter ions. Hence, a pharmaceutically acceptable salt can have one or more charged atoms in the parent compound and/or one or more counter ions.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When a provided compound is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminium, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylaminetripropylamine, tromethamine and the like. Quartemary ammonium salts such as $N^+(C_{1-4}\ alkyl)_4$ are also included.

The preparation of the pharmaceutically acceptable salts described above and other typical pharmaceutically acceptable salts is more fully described by Berge et al., "Pharmaceutical Salts," *J. Pharm. Sci.*, 1977:66:1-19.

The formulations of 10-HDA, or compositions comprising 10-HDA, described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising 10-HDA and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

It will be appreciated that any compound that is a prodrug of 10-HDA, is also within the scope and spirit of the invention. The term "pro-drug" is used in its broadest sense and encompasses those derivatives that are converted in vivo to the compounds of the invention. Such derivatives would readily occur to those skilled in the art.

Furthermore, it is recognised that 10-HDA may be in crystalline form either as the free compound or as a solvate (e.g., hydrates) and it is intended that both forms are within the scope of the present invention. Methods of solvation are generally known within the art.

It is further recognised that is light of its structure, 10-HDA in accordance with the present invention may be capable of undergoing tautomerism. Accordingly, all possible tautomers of 10-HDA of the present invention fall within the scope and spirit of the invention.

As used herein, the term "derived from" shall be taken to indicate that a particular integer or group of integers has originated from the species specified, but has not necessarily been obtained directly from the specified source. For example, it is understood that 10-HDA may have originated from royal jelly, but has not necessarily been obtained directly from the specified source. Further, as used herein the singular forms of "a", "and" and "the" include plural referents unless the context clearly dictates otherwise.

Those skilled in the art will be aware that the invention described herein is subject to variations and modifications other than those specifically described. It is to be understood that the invention described herein includes all such variations and modifications. The invention also includes all such steps, features, methods, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Certain embodiments of the invention will now be described with reference to the following examples which are intended for the purpose of illustration only and are not intended to limit the scope of the generality hereinbefore described.

EXAMPLES

Example 1

Effects of BPA and 10-HDA on Aromatase Expression on Human Neuronal Cells

Human neuroblastoma SHY-SY-5Y cells were cultured were cultured in Dulbecco's Modified Eagle Medium supplemented with 10% heat-inactivated Fetal Bovine Serum, 1% penicillin and 1% L-Glutamine at 37° C. in a humidified atmosphere of 95% air and 5% CO2. The localization of aromatase in these cells can be detected using immunohistochemistry with antibody specific to aromatase. Under normal conditions, aromatase appears as punctuate staining throughout the cells, as it is a membrane bound protein in the endoplasmic reticulum. In the presence of 25 μg/L of bisphenol A (BPA), aromatase forms aggregate and will lose its function. The addition of 10-HDA can protect against the denaturing effect of bisphenol A on aromatase. These results demonstrated the adverse effects of aromatase in cells and the protective effects of 10-HDA on aromatase.

Example 2

In Vivo Mouse Models

Aromatase is expressed in high levels in the mouse medial amygdala and the same region is activated by interaction with a stranger mouse. In humans, aromatase is also highly expressed in the amygdala and fMRI studies suggest that the amygdala is less activated in people with ASD than controls. It was postulated that an Aromatase Knockout mouse (ArKO) model may exhibit behavioural phenotypes reflective of some of the key diagnostic behaviours and symptoms of ASD, including, for example ASD-like behavioural disturbances.

Figure 2:
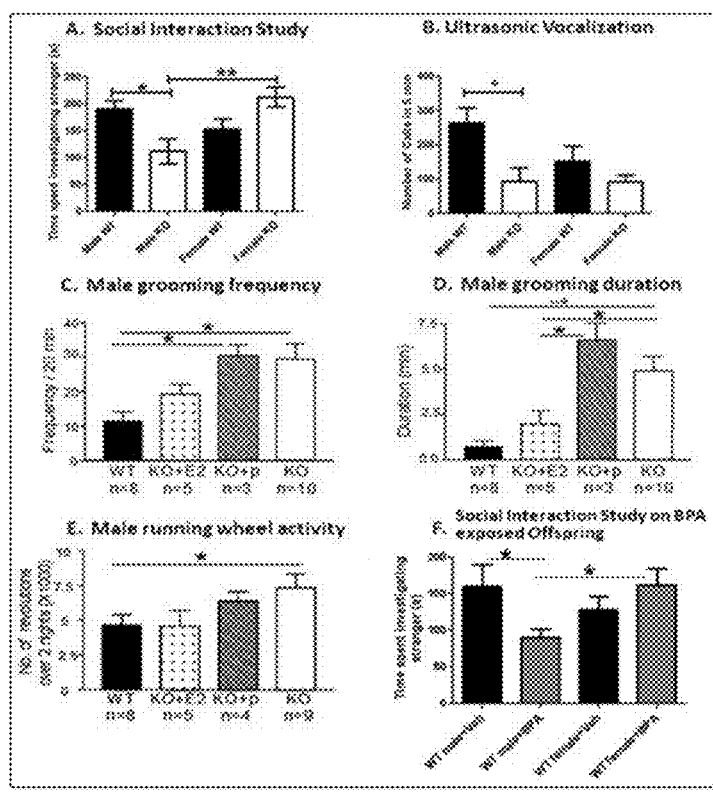
FIG. 2: Autistic-like behaviour of male ArKO and BPA exposed mice. A. Social interaction study; B. Ultrasonic vocalization; C. Male grooming frequency; D. Male grooming duration; E. Make running wheel activity; and F. Social interaction study on BPA exposed offspring.

Accordingly, an aromatase deficient mouse model (ArKO) was developed which presents the core autistic-like features, including vocalization deficit, compulsive grooming, and social interaction deficit (FIG. 2; A to E). When aromatase is knocked out, testosterone accumulates in the serum of ArKO mice and cannot be lowered by estrogen receptor agonists.

Specifically, the inventors have found that the lack of a normal functioning aromatase will precipitate the following ASD-like behavioural disturbances in the male ArKO (aromatase knockout) mouse, but not in the female ArKO mouse:

i) Abnormal Social interaction (FIG. 2A): Juvenile (4 week-old) male ArKO mice were found to spend significantly less time investigating the stranger mouse than wild-type male mouse (WT). Conversely, the female ArKO and WT mice were found to spend similar amounts of time with the stranger mouse.

ii) Ultrasonic vocalization deficit (FIG. 2B): Male ArKO 9-day old pups were found to vocalize significantly less than male WT litter mates when separated from their litters iii) Repetitive behaviour: Male ArKO mice were found to groom more frequently (FIG. 2C) and for longer periods of time (FIG. 2D), when compared with WT and female ArKO mice, as measured during 20 minute period after administering a water mist spray. Male ArKO mice were also found to spend significantly more time on the running wheel when compared with WT and female ArKO mice (FIG. 2E).

The inventors have demonstrated that bisphenol A (BPA) (employed in the preparation of polycarbonate plastics and epoxy resins) could denature aromatase in vitro (FIG. 1). Accordingly, a further study was conducted to examine the role of environmental exposure to Bisphenol A (BPA) in the subsequent development of autistic-like behaviour. In further studies examining the effects of exposure to BPA, the ArKO mouse, which presents core ASD-like features, was used as a comparison.

Figure 3:
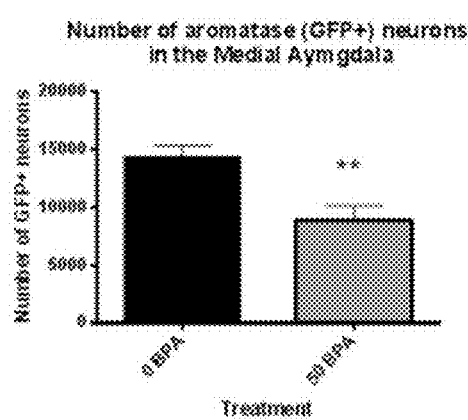
FIG. 3: Effects of BPA exposure on aromatase-GFP positive neurons in utero, counted by standard Stereology method.

BPA (50 μg/kg) was thus administered to pregnant mice mid-gestation (i.e. embryonic days 10.5 to 14.5). The resultant WT male offspring were found to exhibit ASD-like behaviours, similar to those of the male ArKO mice (FIG. 2F). Specifically, male offspring spent significantly less time with the stranger mice than either the control male offspring (vehicle exposed) or the BPA exposed female offspring. Additionally, male offspring exposed to BPA were found to have 13.5% fewer neurons in the medial amygdala, which is in accordance with the ~15% decrease in neuronal numbers observed in the amygdala of adolescent and adult autistic brains, as detected by the post-mortem stereology. A further study was conducted to examine the effects of BPA exposure on numbers of aromatase-GFP positive neurons in utero (FIG. 3). The medial amygdala is involved in social interaction and highly expressed aromatase. Following exposure to BPA, it was found that the numbers of aromatase-GFP positive neurons were significantly reduced, as counted by standard Stereology method

Example 4

In Vivo Mouse Model Treated with 10-HDA

As described in Example 2, mice with autistic-like behaviour were generated by mating female wild type FVBN mice with male CYP19-GFP mice and followed by subcutaneous injection of 50 µg/day of BPA on gestational days 10.5 to 14.5.

After weaning, control and BPA exposed pups were administered 10-HDA daily (0 and 500 µg/kg/day; dissolved in saline) by intraperitoneal injection for a maximum period of 6 weeks. Six litters were initially studied after 3 weeks of daily treatment for anxiety, memory, social interaction (FIG. 4A) and spontaneous grooming.

Data collection was conducted by investigators who were blind to the respective genotypes or treatment of any given animal. Two criteria were assessed as the basis for the behavioural studies, social interaction, and spontaneous grooming activity.

With regard to the social interaction study, the test mouse was placed in a social test box, a three-chambered clear plastic box with doorways in the dividing walls to allow access into each chamber. Each side-chamber contained a wire cage. The test mouse was evaluated over three sessions. In session 1, the test mouse was placed in the middle chamber and allowed to explore all 3 chambers for 10 min. In session 2, an unfamiliar same sex and age mouse (stranger 1) was enclosed in the wire cage either side of the central chamber, and the test mouse was allowed to explore the entire social test box for a period of 10 min. In session 3, a new unfamiliar mouse was placed in the previously empty wire cage such that the test mouse has a choice between the first, now familiar, already-investigated mouse (stranger 1) and the novel unfamiliar mouse (stranger 2). Mouse movements were recorded and tracked using the TopScan video tracking system. Durations in each chamber, time spent sniffing each wire cage, and the number of transitions between chambers were analysed.

Spontaneous Grooming activity was used as a measure of repetitive activity. The spontaneous grooming of the mice were recorded by the TopScan video tracking system during the session 1 or the 3 chamber studies described above. The duration and frequency of grooming were the parameters of measurements and analysed blind.

Figure 4:
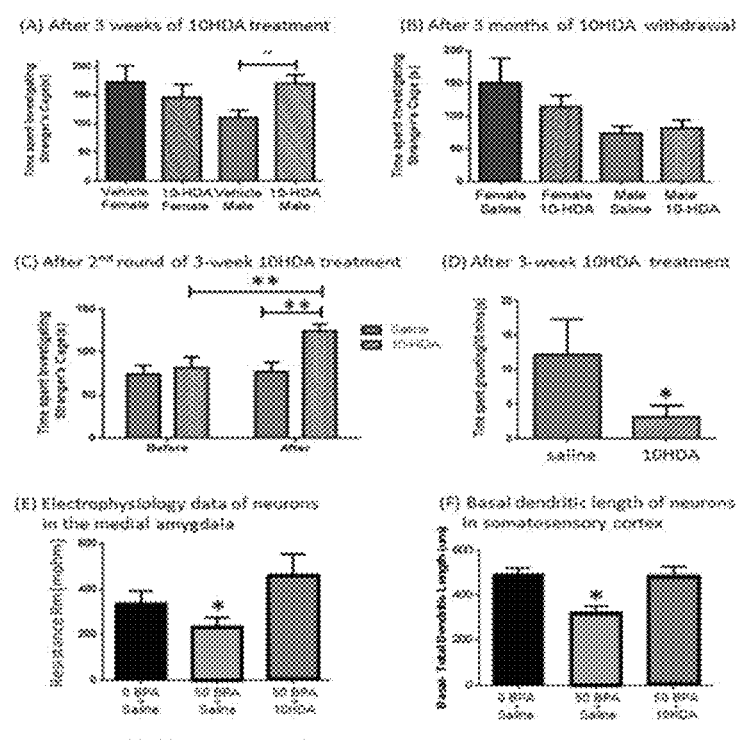
FIG. 4: Social interaction and electrophysiology/dendritic length study of the effects of 10-HDA on BPA exposed mice. A. Daily injection of 10-HDA to male BPA-exposed mice after weaning; B. 3 months after withdrawing 10-HDA treatment; C. Subsequent re-administration of 10-HDA after initial withdrawal; D. Excessive grooming observed in BPA exposed male offspring after 3 week 10-HDA treatment; E. Resistance of neurons in the medial amygdala in control, BPA and BPE+10-HDA treated mice; and F. Basal dendritic length of neurons in control, BPA and BPE+10-HDA treated mice.
Figure 5:
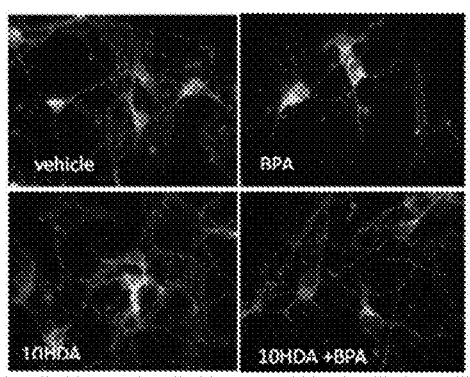
FIGS. 5-9: In vitro analysis of effects of BPA and 10-HDA in primary cortical cell cultures of male mouse embryonic foetuses.
Figure 6:
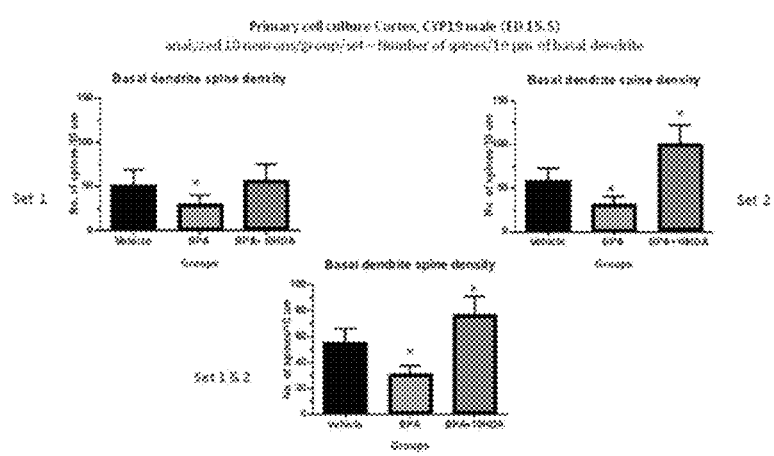
Figure 7:
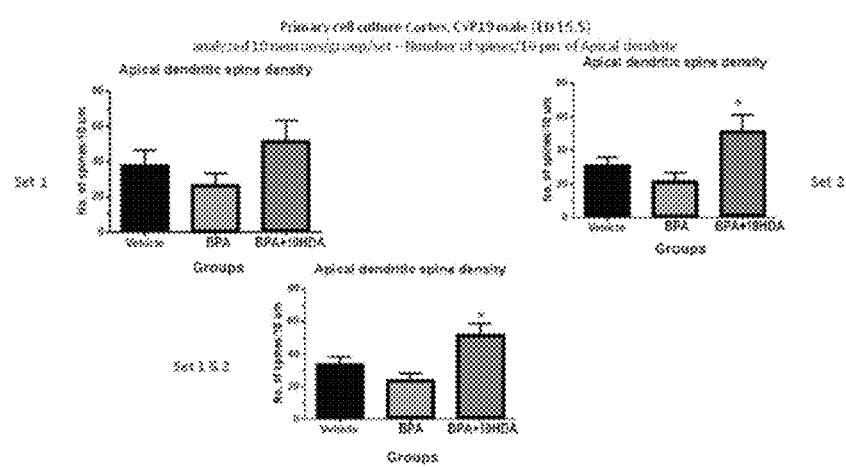
Figure 8:
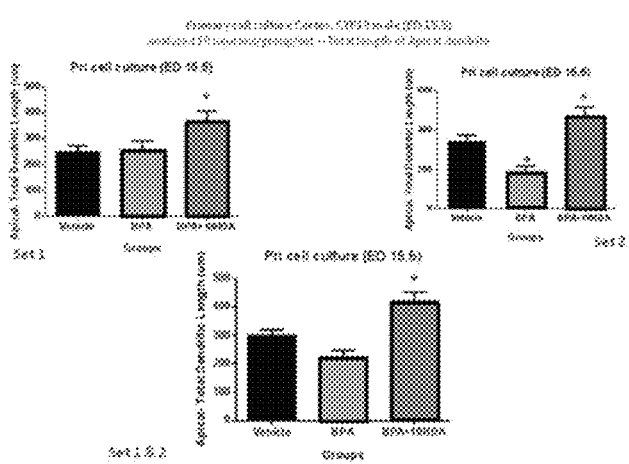
Figure 9:
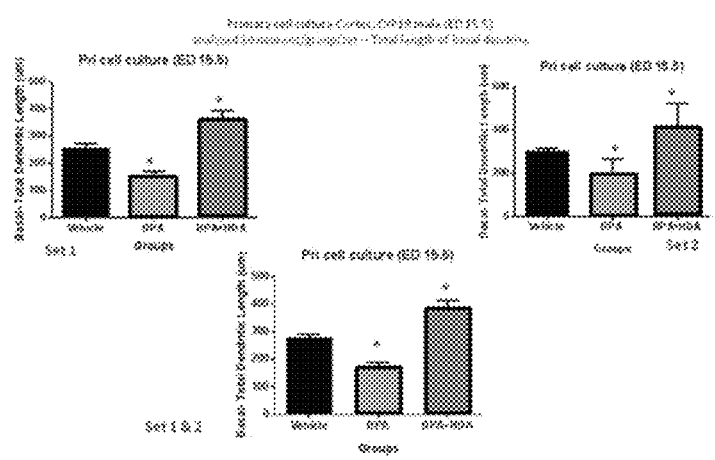
Figure 10:
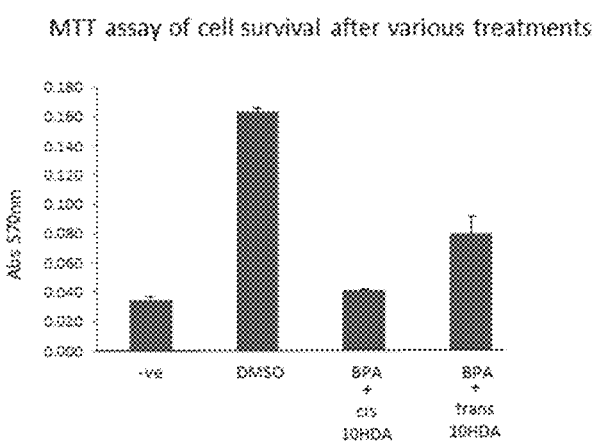
FIG. 10: Bar graph showing comparison of cis and trans 10-HDA activity in protecting NSC-34 cells from toxic BPA exposure, where DMSO reflects cells exposed to DMSO vehicle only and –ve reflects the negative control cells exposed to BPA in the absence of 10-HDA.

After behavioural testing, all treatments were withdrawn for 3 months, and behaviour of the animals was tested again (FIG. 4B) showing that 10HDA treatment withdrawal led to presentation of social interaction deficit in BPA-exposed male animals. The male animals were then re-administered with either vehicle or 10-HDA as described above for 3 weeks, and subjected to behavioural studies again (FIG. 4C). The excessive grooming observed in the 50 µg/kg/day of BPA exposed male offspring was ameliorated by the 10-HDA treatment (FIG. 4D). The results demonstrated that 10-HDA could ameliorate the social interaction deficit and autistic-like behaviour in BPA exposed animals.

After behaviour studies, the animals were sacrificed and electrophysiological data were gathered from the brain slices by patch clamping of aromatase cells in the amygdala. It was demonstrated that BPA exposure reduced the resistance of the neurons and 10-HDA treatment restored resistance to normal (FIG. 4E). 10-HDA treatment also restored the dendritic length of the neurons in the somatosensory cortex to normal length (FIG. 4F).

Example 5

In Vitro Analysis of Effects of BPA and 10-HDA in Primary Cortical Cell Cultures of Male Mouse Embryonic Foetuses Primary cortical culture was prepared from male mouse foetuses at embryonic day 15.5. Specifically, the effects of BPA and 10-HDA on dendritic length and spine densities were assessed. Four test groups were assessed, mice treated with BPA, mice treated with 10-HDA, mice treated with BPA and 10-HDA, and a vehicle control. Ten neurons were measured and the experiments were duplicated. Results indicated that BPA decreased the spine density as well as the dendritic length of neurons. 10-HDA was found to reverse or protect against the effect of BPA. Results are presented in FIGS. 5 to 9. The results demonstrated that 10-HDA has the capacity to stimulate neurites and spines formation This is significant given that most genes linked to Autism were engaged in regulation of neurite outgrowth ("A noise-reduction GWAS analysis implicates altered regulation of neurite outgrowth and guidance in autism", Hussman J P, et al, *Mol Autism*. 2011 Jan. 19; 2(1):1.

Example 6

Comparison of Trans 10-HDA and Cis 10-HDA Activity

To compare the respective activities of trans and cis 10-HDA 1 mM respectively of cis or trans 10-HDA in the presence of 500 ng/ml of BPA (toxic level) was added to differentiated mouse motor neuronal NSC-34 cells. Cell survival was determined by MTT assay 72 hours later. The results demonstrated that cis 10-HDA does not protect against BP toxicity, whereas trans 10-HDA exhibits neuroprotective effects.

The invention claimed is:

1. A method for the treatment of a disease or disorder of the central nervous system, comprising administering to a mammal in need thereof an effective amount of trans 10-hydroxy-2-decenoic acid or a pharmaceutically acceptable salt thereof, wherein the trans 10-hydroxy-2-decenoic acid or a pharmaceutically acceptable salt thereof is administered in a dosage in the range of 0.01 to 6000 mg/day.

2. The method according to claim 1, wherein the disease or disorder is a neurodevelopmental disease or disorder.

3. The method according to claim 1 wherein the disease or disorder is an acquired neurodevelopmental disease or disorder, a congenital neurodevelopmental disease or disorder, or a related condition.

4. The method according to claim 1, wherein the disease or disorder is an autism spectrum disorder.

5. The method according to claim 4 wherein the autism spectrum disorder is selected from the group consisting of Autistic Disorder, Asperger's Disorder, Childhood Disintegrative Disorder and Pervasive Developmental Disorder-Not Otherwise Specified, and Rett syndrome.

6. The method according to claim 1, wherein the trans 10-hydroxy-2-decenoic acid or a pharmaceutically acceptable salt thereof is administered as a composition.

7. The method according to claim 6 wherein the composition comprises royal jelly, an extract of royal jelly, or a composition derived from royal jelly.

8. The method according to claim 1, wherein the trans 10-hydroxy-2-decenoic acid or a pharmaceutically acceptable salt thereof is administered in a dosage in the range of 100 to 2000 mg/day.

9. A method for the treatment of a neurodevelopmental disease or disorder, comprising administration of a therapeutic agent, wherein the agent is trans 10-hydroxy-2-decenoic acid or a pharmaceutically acceptable salt thereof.

10. The method of claim 9 wherein the disease or disorder is selected from the group consisting of Autistic Disorder, Asperger's Disorder, Childhood Disintegrative Disorder and Pervasive Developmental Disorder-Not Otherwise Specified, and Rett syndrome.

11. The method of claim 9, wherein the trans 10-hydroxy-2-decenoic acid, or a pharmaceutically acceptable salt thereof, is administered as a pharmaceutically acceptable dosage form in the range of 0.01 mg/day to 6000 mg/day.

12. The method of claim 10, wherein the trans 10-hydroxy-2-decenoic acid, or a pharmaceutically acceptable salt thereof, is administered as a pharmaceutically acceptable dosage form in the range of 0.01 mg/day to 6000 mg/day.

* * * * *